United States Patent [19]

Szabolcs

[11] Patent Number: 4,467,122
[45] Date of Patent: Aug. 21, 1984

[54] CONDENSATION PROCESS

[75] Inventor: Otto Szabolcs, Vienna, Austria

[73] Assignee: Isovolta Osterreichische Isolierstoffwerke Aktiengesellschaft, Wiener Neudorf, Austria

[21] Appl. No.: 379,433

[22] Filed: May 18, 1982

Related U.S. Application Data

[63] Continuation-in-part of Ser. No. 250,669, Apr. 3, 1981, abandoned, which is a continuation-in-part of Ser. No. 083,609, Oct. 11, 1979, abandoned.

[51] Int. Cl.$^3$ .............................................. C07C 37/20
[52] U.S. Cl. ..................................... 568/727; 568/722
[58] Field of Search ....................... 568/719, 727, 722

[56] References Cited

U.S. PATENT DOCUMENTS

| | | | |
|---|---|---|---|
| 2,468,982 | 5/1949 | Jansen | 568/727 |
| 2,542,688 | 2/1951 | Johnson et al. | 568/727 |
| 2,730,553 | 1/1956 | Williamson | 568/727 |
| 2,775,620 | 12/1956 | Williamson | 568/727 |
| 2,936,272 | 5/1960 | Bender | 568/727 |
| 3,207,794 | 9/1965 | Haines | 568/727 |
| 3,367,979 | 2/1968 | Harper et al. | 568/727 |
| 3,546,165 | 11/1970 | Morgan | 568/727 |

*Primary Examiner*—James H. Reamer
*Attorney, Agent, or Firm*—Charles A. Muserlian

[57] ABSTRACT

In a process for the preparation of phenol-aromatic ketone condensation products by reaction of phenols and ketones in the presence of a gaseous hydrogen halide, the improvement comprising adding in catalytic amounts up to less than molar amounts based on the ketone as an additional condensation agent at least one bivalent, trivalent or tetravalent metal halide, introducing the gaseous hydrogen halide and after termination of the condensation reaction, adding water to the reaction mixture and recovering the purified condensation product and to the novel monomers of 9,9-bis-(4-hydroxyphenyl)-fluorene with a melting point of at least 226° C. and 1,1-bis-(4-hydroxyphenyl)-1-phenylethene with melting point of at least 189° C. which are useful for the preparation of improved polyester resins.

16 Claims, No Drawings

CONDENSATION PROCESS

PRIOR APPLICATION

This application is a continuation-in-part of my copending, commonly assigned U.S. patent application Ser. No. 250,669 filed Apr. 3, 1981, now abandoned which in turn is a continuation-in-part application of copending, commonly assigned U.S. patent application Ser. No. 83,609 filed Oct. 11, 1979, now abandoned.

STATE OF THE ART

Phenol-ketone condensation products, especially so-called bisphenols, are used extensively in the plastic industry, especially as monomers in polycondensation processes. The said condensation products are normally prepared by condensation of the anhydrous ketone and anhydrous phenol in the presence of gaseous hydrogen halide, especially hydrogen chloride.

In one process of this type, the ketone is dissolved in the molten phenol and then gaseous hydrogen chloride is added to the solution as a condensation agent. Usually more than 2 moles, preferably 2.5 to 5 moles, of phenol per mole of ketone are used which corresponds to a molar excess 0.5 to 3 moles of phenol. The excess phenol is employed to keep the reaction mixture in a stirrable liquid to pasty state at the end of the condensation reaction. In subsequent processing, the excess phenol must be removed from the condensation product and the expense thereof increases with the amount of excess phenols.

Another disadvantage of the prior art processes are the side reactions which frequently occur when more complex ketones in their hydrocarbon moiety are used since the desired bisphenol is often difficult to separate from the reaction products of the side reactions. Ketones of this nature include fluorenone, acetophenone, hexafluoroacetone and the like. The degree of side reaction increases with the rise in reaction temperatures and therefore the condensation reactions are carried out under the mildest reaction conditions, i.e., the lowest possible temperatures which require extremely long reaction times on the order of several days.

OBJECTS OF THE INVENTION

It is an object of the invention to provide an improved process for the condensation of phenols and ketones with reduced reaction times and improved purification steps.

It is another object of the invention to provide a phenol-ketone condensation process wherein the condensation agent is a mixture of gaseous hydrogen halide and at least one divalent, trivalent or tetravalent metal halide.

It is a further object of the invention to provide more pure 9,9-bis-(4-hydroxhphenyl)-fluorene and 1,1-bis-(4-hydroxyphenyl)-1-phenylethene useful for the preparation of superior polyester resins.

These and other objects and advantages of the invention will become obvious from the following detailed description.

THE INVENTION

The novel process of the invention for the preparation of a phenol-ketone condensation product comprises forming a liquid mixture of a monohydric phenol and an aromatic ketone and a catalytic amount up to less than molar amount based on ketone as an additional condensation agent at least one bivalent, trivalent or tetravalent halide, adding gaseous hydrogen halide to the liquid mixture to effect the condensation, reacting the completed reaction mixture with water whereby the condensation product precipitates, washing the latter and recovering the purified condensation product.

The condensation reaction is preferably effected under mild reaction conditons, i.e., below 100° C., preferably at 20° to 85° C., most preferably 40° to 70° C., and the precipitated condensation product is preferably washed with boiling water and then optionally with another hot aqueous alkaline solvent, then dried and subjected to further purification.

Preferably, more than 2 moles of phenol per mole of ketone are used in the reaction, preferably 2.5 to 5 moles of phenol and the ketone and the metal halide are dissolved in the phenol. In another preferred embodiment of the process, steam is passed through the completed reaction mixture to supply the water and to at least partially remove the excess phenol. In a preferred embodiment, the reaction mixture is dissolved in isopropanol heated to 60° C. and the solution is then poured with vigorous stirring into 10 volumes of water to precipitate the bisphenol. The water washing may be effected by addition of water to the reaction mixture to cause precipitation and then centrifuging the mixture while washing with hot water or passing steam therethrough.

The metal halides are preferably the chlorides of metals of groups IIA, IIB, IIIA, IVA, IVB and VIIIB of the Periodic Table. Examples of specific metal halides are dichlorides such as calcium chloride, zinc chloride, etc., trichlorides such as ferric chloride and aluminum trichlororide and tetrachlorides such as titanium tetrachloride and tin tetrachloride. The metal chlorides may be used individually or in mixtures and the amount of metal halide used is 0.03 to 0.5, preferably 0.1 to 0.3, moles per mole of ketone.

The washed condensation product is preferably further purified by dissolution in a halogenated organic solvent, crystallizing the product at low temperatures, washing the product with cold halogenated organic solvent and drying the latter to form a purified condensation product. The preferred chlorinated organic solvent is 1,2-dichloroethane.

Preferably, the condensation of the phenol and the ketone is effected under anhydrous conditions at the start of the reaction but up to 15% by weight of water may be present in the reaction mixture as water is continuously formed during the reaction.

The phenols and ketones used in the condensation are well known and are described in the literature such as U.S. Pat. No. 2,468,982. Various substituted phenols may be used but phenol per se is preferred. The ketones are well known and preferably one of the hydrocarbon groups of the ketone contains an aryl group, i.e. phenyl or the hydrocarbon radicals connected to the carbonyl groups of the ketone form a bivalent aromatic group. Examples of specific ketone are fluoroenone, acetophenone and hexafluoroacetone.

The novel pure compounds of the invention are 9,9-bis-(4-hydroxy phenyl)-fluorine with a melting point of at least 226° C., preferably 228 to 230° C. and 1,1-bis-(4-hydroxyphenyl)-1-phenylethane with a melting point at least 189° C., preferably 189° to 191° C. and have the unexpected advantage of being useful for the preparation of high-molecular weight aromatic polyesters with terephthalic and/or isophthalic acid having superior properties to prior art polyesters for the electric insulation field including films with improved tear elongation properties, thermal stability, solvent resistance and electrical insulation properties.

In the following examples there are described several preferred embodiments to illustrate the invention. However, it is to be understood that the invention is not intended to be limited to the preferred embodiments.

EXAMPLE 1

Preparation of 9,9-bis-(4-hydroxyphenyl)-fluorene 50 kg (532 moles) of phenol were melted in a 250 liter autoclave equipped with a strong stirrer and then 2.7 kg (20 moles) of zinc chloride and 36 kg (200 moles) of fluorenone were dissolved at 60° C. in the phenol. 2.4 kg (66 moles) of gaseous hydrogen chloride were added to the stirred mixture over 8 hours at 60° C. and the mixture was then stirred for another 16 hours to complete the reaction. The resulting mixture in the form of a light-colored crystalline paste was diluted in the autoclave by stirring with hot water which caused small additional amounts of precipitate to occur. The resulting mixture was centrifuged and was washed with boiling water while centrifuging to remove hydrochloric acid, zinc chloride and excess phenol. The white crystalline product was vacuum dried at 100° C. to obtain 67 kg (96% yield) of crude 9,9-bis-(4-hydroxyphenyl)-fluorene.

The said product was dissolved in 500 liters of refluxing 1,2-dichloroethane (b.p.=84° C.) in a heatable and coolable closed vessel equipped with a stirrer and the resulting solution was treated with activated carbon and was cooled to 0° C. with constant stirring during which the bisphenol crystallized. The mixture was centrifuged and was washed with cold 1,2-dichloroethane and the recovered product was vacuum dried at 100° C. to obtain 60 kg (86% yield) to pure 9,9-bis-(4-hydroxyphenol)-fluorene melting at 228°–230° C. The purity determined by high pressure liquid chromatography was 99.8%. The single crystallization purification step was possible since unreacted starting material and by-product were almost completely removed during processing.

EXAMPLE 2

Preparation of 1,1-bis-(4-hydroxyphenyl)-1-phenylethane

The process of Example 1 was repeated with 24 kg (200 moles) of acetophenone, 40 kg (426 moles) of phenol, 2.7 kg (20 moles) of zinc chloride and 2.4 g (66 moles) of gaseous hydrogen chloride. After 8 hours of addition of hydrogen chloride and 40 hours of stirring to complete the reaction, a light colored, crystalline paste was obtained which was treated as in Example 1 to obtain 55 kg (95% yield) of crude 1,1-bis-(4-hydroxyphenyl)-1-phenylethane in the form of weakly-colored crystals. The said product was purified with 600 liters of 1,2-dichloroethane as in Example 1 to obtain 49 kg (84% yield) of 1,1-bis-(4-hydroxyphenyl)-1-phenylethane melting at 189°–191° C. The purity of the product determined by high pressure liquid chromatography was greater than 99.8%.

EXAMPLE 3

9,9-bis-(4-hydroxyphenyl)-fluorene 30 moles of phenol containing 9% by weight of water were stirred in an autoclave and then 2 moles of zinc chloride and 10 moles of fluorenone were dissolved therein. Then, 10 moles of gaseous hydrogen chloride were added to the stirred mixture and the mixture was reacted at 80° C. for one hour and then at 70° C. for 3 hours. The reaction mixture was then dissolved in 5 liters of isopropanol at 60° C. and the solution was then poured with vigorous stirring into a ten-fold volume of water whereby the resulting bisphenol precipitated as 3.4 kg (97% yield) of the product in the form of a yellow product.

EXAMPLE 4

9,9-bis-(4-hydroxyphenyl)-fluorene 20 moles of phenol containing 9% by weight of water were stirred in an autoclave and then one mole of zinc chloride and 10 moles of fluorenone were dissolved therein. Then, 5 moles of gaseous hydrogen chloride were added to the stirred mixture and the mixture was reacted at 70° C. for 4 hours. The reaction mixture was then dissolved in 5 liters of isopropanol at 60° C. and the solution was poured with vigorous stirring into a ten-fold volume of water to precipitate 3.4 kg of 9,9,-bis-(4-hydroxyphenyl)-fluorene (97% yield in the form of a yellow product.

EXAMPLE 5

9,9-bis-(4-hydroxyphenyl)-fluorene 40 moles of phenol containing 9% by weight of water were stirred in an autoclave and 2 moles of zinc chloride and 10 moles of fluorenone were dissolved therein. Then, 10 moles of gaseous hydrogen chloride were added and the mixture was reacted for 4 days at room temperature. The reaction mixture was dissolved in 5 liters of isopropanol at 60° C. and the solution was poured with vigorous stirring into 10 fold volume of water to obtain 3,4 kg of 9,9-bis-(4-hydroxyphenyl)-fluorene (97% yield) in the form of a light-yellow product of greater purity than Examples 3 and 4.

EXAMPLE 6

9,9-bis-(4-hydroxyphenyl)-fluorene 15 moles of phenol containing 9% by weight of water were stirred in an autoclave at 50° C. and then one mole of zinc chloride and 5 moles of fluorenone were dissolved therein. The mixture was saturated with gaseous hydrogen chloride and the mixture was reacted at room temperature for 2 days. The mixture was dissolved in 2.5 liters of isopropanol at 60° C. and the solution was poured with vigorous stirring into a 10 fold volume of water to obtain 1.6 kg (92% yield) of the desired bisphenol in the form of a light yellow product. Crystallization from toluene gave an 81% yield of crystalline product with a purity equal to that of Example 5.

Various modifications of the products and process of the invention may be made without departing from the spirit or scope thereof and it is to be understood that the invention is intended to be limited only as defined in the appended claims.

What I claim is:

1. In a process for the preparation of phenol-aromatic ketone condensation products by reaction of phenols and ketones in the presence of a gaseous hydrogen halide, the improvement consisting essentially of adding in catalytic amounts up to less than molar amounts based on the ketone as an additional condensation agent at least one soluble bivalent, trivalent or tetravalent metal halide of a metal selected from the group consisting of calcium, iron, titanium, zinc, tin and aluminum, in the presence of the gaseous hydrogen halide and after termination of the condensation reaction, adding water to the reaction mixture and recovering the purified condensation product.

2. The process of claim 1 wherein the condensation is effected at 40° to 70° C.

3. The process of claim 1 wherein the hydrogen halide is hydrogen chloride.

4. The process of claim 1 wherein the metal halide is at least one member of the group consisting of $CaCl_2$ and $ZnCl_2$.

5. The process of claim 1 wherein the metal halide is at least one member of the group consisting of $AlCl_3$ and $FeCl_3$.

6. The process of claim 1 wherein the metal halide is at least one member of the group consisting of $SnCl_4$ and $TiCl_4$.

7. The process of claim 1 wherein the amount of metal halide is 0.1 to 0.3 moles per mole of ketone.

8. The process of claim 1 wherein more than two moles of phenol per mole of ketone are employed and the metal halide and the ketone are dissolved in the phenol.

9. The process of claim 1 wherein the reaction mixture is diluted with water and steam is passed through the mixture to at least partially remove excess phenol.

10. The process of claim 1 wherein the condensation product is washed with boiling water and then with a hot aqueous alkaline solution.

11. The process of claim 1 wherein the reaction mixture diluted with water is centrifuged and is then washed therein with water and/or steam.

12. The process of claim 1 wherein the condensation product after washing is crystallized from a chlorinated organic solvent, washed with cold chlorinated organic solvent and dried.

13. The process of claim 12 wherein the solvent is 1,2-dichloroethane.

14. The process of claim 1 wherein up to 10% by weight of water is present during the condensation.

15. The process of claim 1 wherein the condensation is effected under substantially anhydrous conditions.

16. A process for the preparation of a phenol-ketone condensation product consisting esssentially of dissolving an aromatic ketone and a catalytic amount up to less than one mole per mole of ketone of at least one metal chloride selected from the group consisting of $CaCl_2$, $ZnCl_2$, $AlCl_3$, $FeCl_3$, $SnCl_4$ and $TiCl_4$ in more than 2 moles of monohydric phenol per mole of ketone, adding hydrogen chloride to the solution at 40° to 80° C. to effect the condensation, adding water to the complete condensation mixture to precipitate the condensation product, separating the condensation product and washing the same with hot water, crystallizing the product from a chlorinated hydrocarbon solvent and drying the condensation product.

* * * * *